(12) United States Patent
McDonald

(10) Patent No.: US 8,322,026 B2
(45) Date of Patent: Dec. 4, 2012

(54) METHOD FOR FORMING A LEAD

(75) Inventor: Matthew Lee McDonald, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 637 days.

(21) Appl. No.: 12/494,086

(22) Filed: Jun. 29, 2009

(65) Prior Publication Data

US 2010/0326701 A1     Dec. 30, 2010

(51) Int. Cl.
*H01R 43/00* (2006.01)

(52) U.S. Cl. ............... 29/825; 29/846; 29/848; 29/850; 29/884; 607/116

(58) Field of Classification Search ............ 29/825, 29/846, 848, 850, 884; 607/116
See application file for complete search history.

(56) References Cited

U.S. PATENT DOCUMENTS

| | | | |
|---|---|---|---|
| 5,408,738 A * | 4/1995 | Schantz et al. ............ | 29/611 |
| 5,604,976 A | 2/1997 | Stobie et al. | |
| 5,782,645 A | 7/1998 | Stobie et al. | |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,757,970 B1 | 7/2004 | Kuzma et al. | |
| 6,981,314 B2 | 1/2006 | Black | |
| 7,231,260 B2 | 6/2007 | Wallace et al. | |
| 7,244,150 B1 | 7/2007 | Brase et al. | |
| 2003/0114905 A1 | 6/2003 | Kuzma | |
| 2004/0059392 A1 | 3/2004 | Parramon et al. | |
| 2005/0165465 A1 | 7/2005 | Pianca et al. | |
| 2005/0251238 A1 | 11/2005 | Wallace et al. | |
| 2005/0251239 A1 * | 11/2005 | Wallace et al. ............ | 607/126 |
| 2006/0265037 A1 | 11/2006 | Kuzma | |
| 2007/0150007 A1 | 6/2007 | Anderson et al. | |

(Continued)

FOREIGN PATENT DOCUMENTS

EP     1742702 A1     1/2007

(Continued)

OTHER PUBLICATIONS

U.S. Appl. No. 11/238,240, filed Sep. 29, 2005.

*Primary Examiner* — Carl Arbes

(74) *Attorney, Agent, or Firm* — Frommer, Lawrence & Haug LLP; Bruce E. Black

(57) ABSTRACT

A method for forming a lead or lead extension includes forming an arrangement of elongated conductors. Each of the conductors extends from a proximal end of the arrangement to a distal end of the arrangement. Each of the conductors includes a layer of insulation disposed over a conductive core. A conductor-separating element is disposed over either the proximal end or the distal end of the arrangement. The conductor-separating element includes a plurality of ablation windows defined in a body. An end of at least one of the elongated conductors is radially extended over a portion of the conductor-separating element such that a portion of the at least one elongated conductor extends across at least one of the ablation windows. Insulation from the portion of the at least one conductor extending across the ablation window is ablated to expose a portion of the conductive core of the elongated conductor.

20 Claims, 12 Drawing Sheets

U.S. PATENT DOCUMENTS

2007/0150036 A1 6/2007 Anderson
2007/0161294 A1 7/2007 Brase et al.
2007/0219595 A1 9/2007 He
2007/0239243 A1 10/2007 Moffitt et al.
2008/0071320 A1 3/2008 Brase

FOREIGN PATENT DOCUMENTS

EP 2016973 A1 1/2009
WO WO-2005110528 A1 11/2005

* cited by examiner

US 8,322,026 B2

METHOD FOR FORMING A LEAD

FIELD

The present invention is directed to the area of implantable electrical stimulation systems and methods of making and using the systems. The present invention is also directed to systems and methods of removing insulation encasing conductors disposed in implantable electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, a method for forming a lead or lead extension includes forming an arrangement of a plurality of elongated conductors. Each conductor extends from a proximal end of the arrangement to a distal end of the arrangement. Each of the plurality of conductors includes a layer of insulation disposed over a conductive core. A conductor-separating element is disposed over one of the proximal end or the distal end of the arrangement. The conductor-separating element includes a plurality of ablation windows defined in a body. An end of at least one of the elongated conductors is radially extended over a portion of the conductor-separating element such that a portion of the at least one elongated conductor extends across at least one of the ablation windows. Insulation from the portion of the at least one conductor extending across the ablation window is ablated to expose a portion of the conductive core of the elongated conductor.

In another embodiment, a conductor-separating element includes a body, a mounting aperture, and a plurality of retention devices. The body defines an outer rim and a plurality of ablation windows disposed circumferentially around the body. The mounting aperture is positioned in a center of the body and is configured and arranged to receive a plurality of elongated conductors. The plurality of retention devices are disposed around the outer rim of the body. Each retention device is configured and arranged to receive, and retain, an end of one of the conductors which passes through the center aperture and is bent over, and extended along, the body of the conductor-separating element. The plurality of ablation windows are positioned such that, when the end of one of the conductors is extended along the body of the conductor-separating element, the conductor has a portion that is exposed entirely around a transverse circumference of the conductor within the ablation window.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to systems and methods of removing insulation encasing conductors disposed in implantable electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent applications Ser. Nos. 10/353,101, 10/503,281, 11/238,240; 11/319,291; 11/327,880; 11/375,638; 11/393,991; and 11/396,309, all of which are incorporated by reference.

Figure 1:
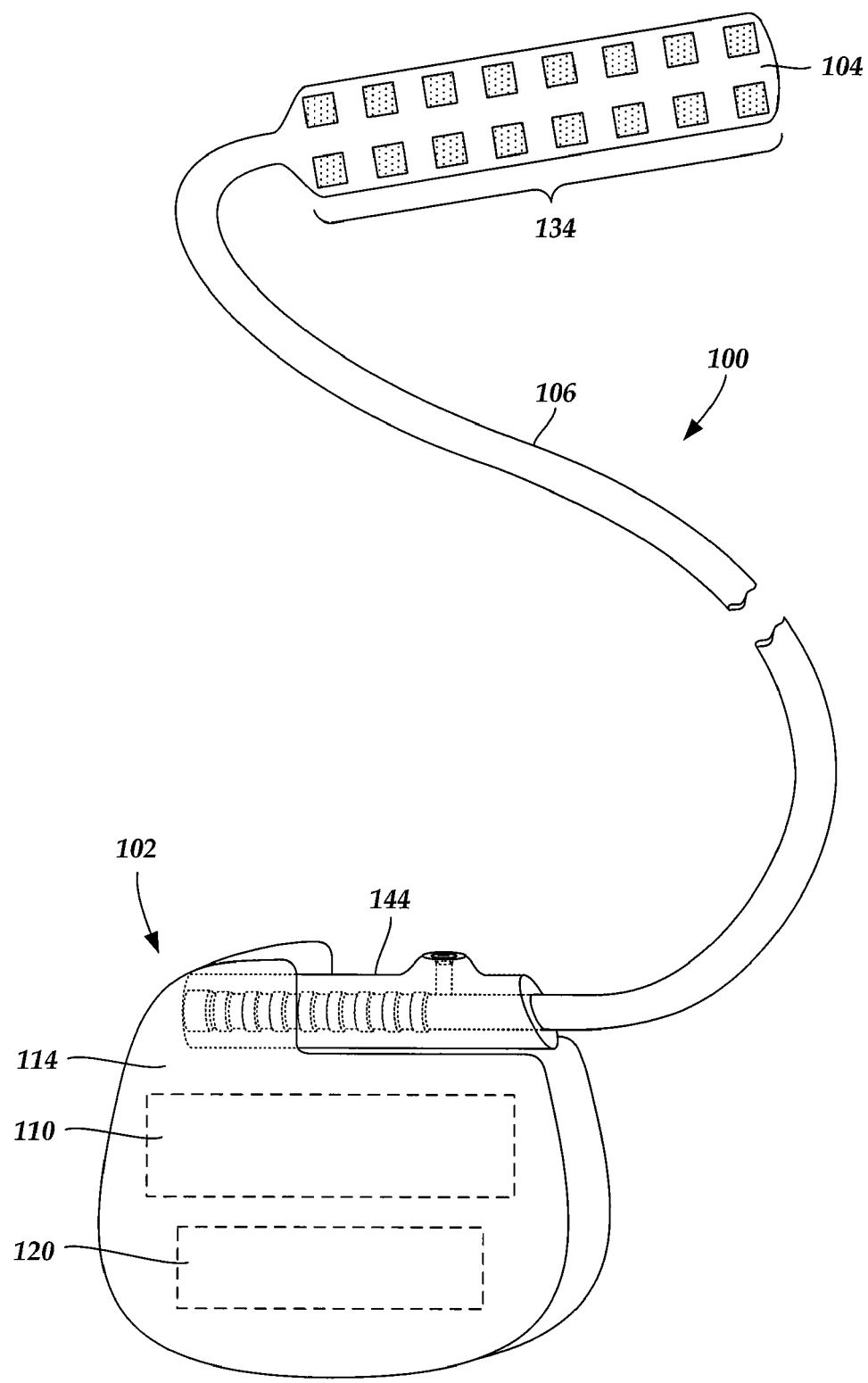
FIG. 1 is a schematic view of one embodiment of an electrical stimulation system, according to the invention.
Figure 2:
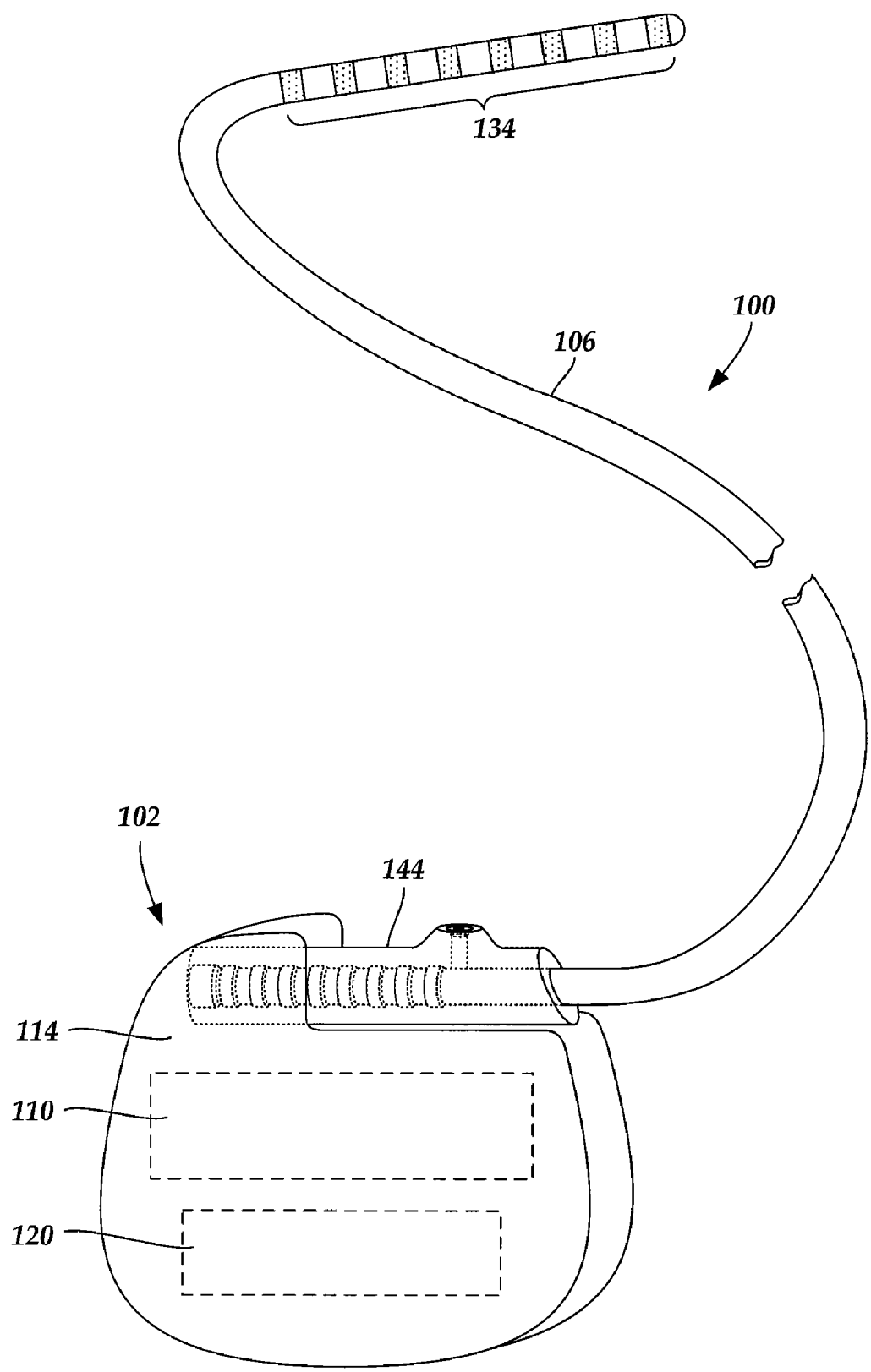
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
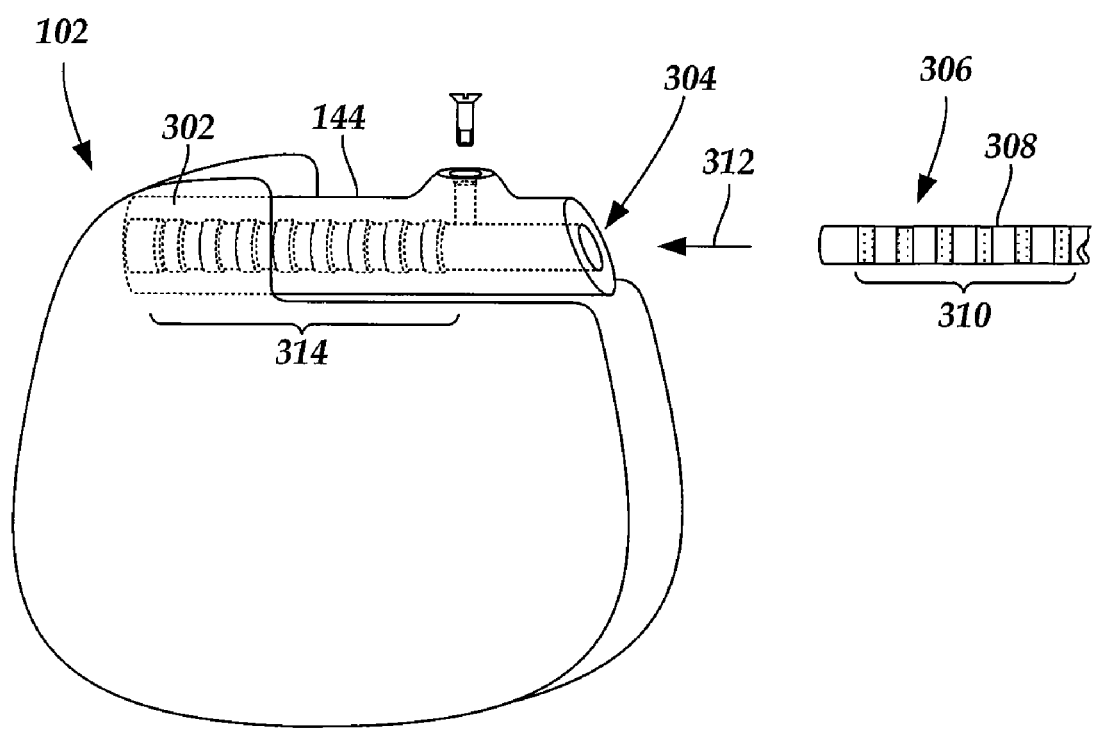
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat.

No. 7,244,150 and U.S. patent application Ser. No. 11/532, 844, which are incorporated by reference.

Figure 3B:
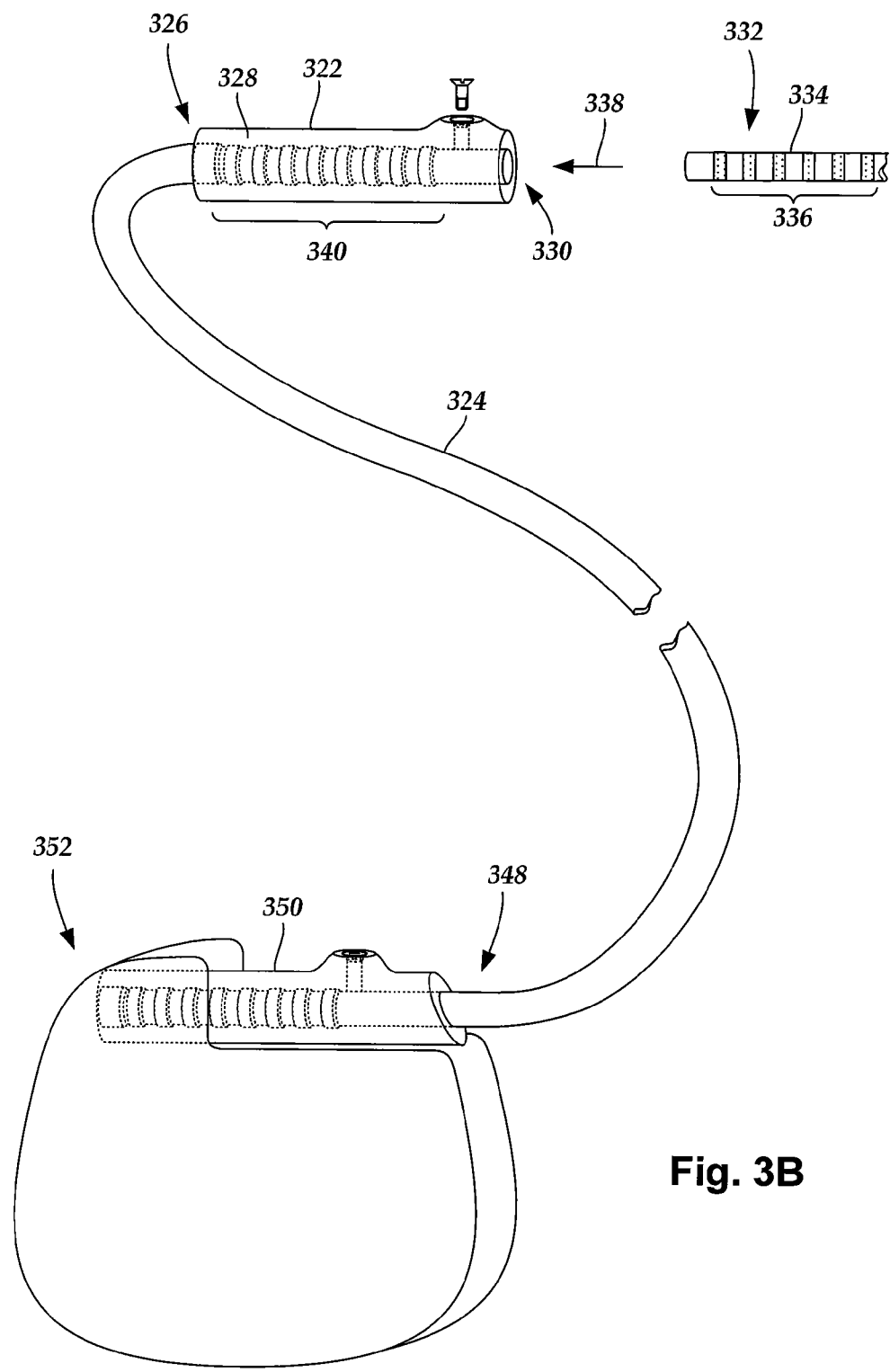
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one terminal to an electrode (or other conductive contact) can be arranged in a conductor path to eliminate or reduce the effect of RF irradiation, such as that generated during magnetic resonance imaging ("MRI"). The conductor path includes a plurality of units arranged in series. In some embodiments, the units are disposed along a single continuous conductor. In other embodiments, the units are separate conductive elements electrically coupled together.

Each unit includes at least three conductor segments that at least partially overlap one another to form a multi-coil region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-coil region flanking at least one end of the multi-coil region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight. In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
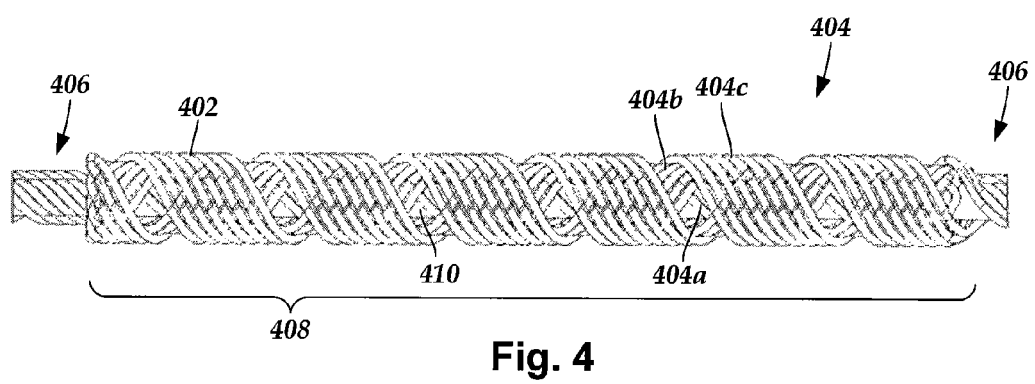
FIG. 4 is a schematic side view of one embodiment of portions of a plurality of conductors disposed along a conductor placement sleeve, the conductors configured into units, according to the invention.

FIG. 4 schematically illustrates one embodiment of a plurality of conductors 402. The conductors 402 are configured into a plurality of units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-coil regions, such as the single-coil regions 406, separated from one another by a multi-coil region, such as the multi-coil region 408.

In at least some embodiments, the conductors 402 are disposed along a conductor placement sleeve 410. The conductor placement sleeve 410 can be formed from any suitable biocompatible material including, for example, one or more polymers. In at least some embodiments, conductor insulation is disposed over the conductors 402 to encapsulate the conductors 402 and electrically isolate the conductors 402 from one another.

In at least some embodiments, one or more conductors having one or more units may be disposed in an elongated member (e.g., a lead or lead extension). In at least some embodiments, the ends of the conductors 402 can be coupled to terminals, electrodes, or conductive contacts. In preferred embodiments, each of the conductors in an elongated member are configured into units. In at least some embodiments, only a subset of the conductors disposed in an elongated member include one or more units, the remaining conductors having a different arrangement (for example, a single conductor segment between the terminal(s) and electrode(s)/conductive contact(s)).

Figure 5:
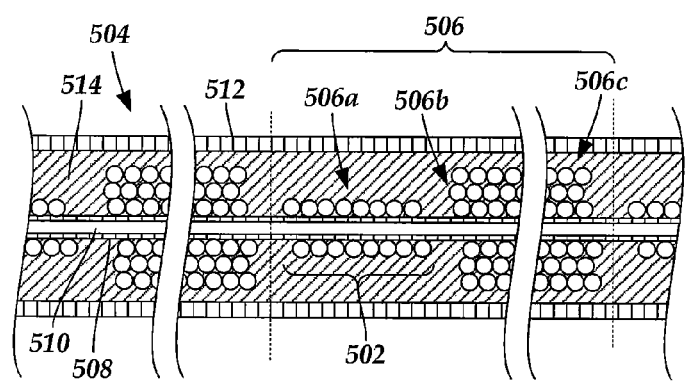
FIG. 5 is a schematic longitudinal cross-sectional view of one embodiment of portions of a plurality of conductors disposed in an elongated member, according to the invention.

Conductors, such as the conductors 402, may be disposed in a lumen of an elongated member (e.g., a lead, lead extension, or the like). FIG. 5 is a schematic longitudinal cross-sectional view of one embodiment of portions of a plurality of conductors 502 disposed in an elongated member 504. The illustrated portions of the conductors 502 includes unit 506, shown between two vertical dotted lines. Unit 506 includes a first conductor segment 506a, a second conductor segment 506b, and a third conductor segment 506c. In at least some embodiments, the conductors 502 are disposed over a conductor placement sleeve 508. In at least some embodiments, the conductor placement sleeve 508 defines a lumen 510. The elongated member 504 includes a body 512 and a lumen 514 into which the conductors 502 are disposed.

As mentioned above, one or more conductors typically extend along at least a portion of the longitudinal length of the elongated member, electrically coupling at least one terminal to an electrode (or other conductive contact). Typically, the conductors are individually encased in a layer of insulation. The number of conductors disposed in the elongated member may vary. Additionally, the conductors in the elongated member may be disposed in many different possible configurations (e.g., arranged into units, coiled into a helical configuration, disposed in a multi-lumen device, disposed over a sleeve, disposed over a mandrel, or the like).

It may be the case that the conductors are pre-fabricated into a body of the elongated member such that each of the conductors is individually encased in the layer of insulation. During formation of the elongated member, the conductors are disposed in the elongated member such that the proximal ends of the conductors extend outward from a proximal end of the outer layer of the elongated member and the distal ends of the conductors extend outward from a distal end of the outer layer of the elongated member. The terminals are then electrically coupled to the proximal ends of the conductors and the electrodes (or conductive contacts) are electrically coupled to the distal ends of the conductors.

The layer of insulation encasing the conductors is removed from a portion of each of the conductors extending from the proximal end of the outer layer of the elongated member so that the proximal ends of the conductors can be coupled to the terminals. Likewise, the layer of insulation encasing the conductors is removed from a portion of each of the conductors extending from the distal end of the outer layer of the elongated member so that the distal ends of the conductors can be coupled to the electrodes (or other conductive contacts). It is preferable to remove as little insulation as is necessary to make electrical contact with the terminal or electrode (or other conductive contact) in order to reduce the chance of electrical shorts. Insulation removal may be difficult when access to the ends of the conductors is at least partially obstructed by other conductors, such as when the conductors are disposed in elaborate configurations or when the conductors are tightly packed in the elongated member.

One technique for insulation removal involves ablating (e.g., laser ablating or the like) the insulation. In some cases, insulation is removed after the conductors are disposed in the elongated member. One difficulty with removing insulation after the conductors are disposed in the elongated member is that ablation techniques typically require line-of-sight access to a complete circumference of the portion of the insulation to be removed, thereby exposing the entire transverse circumference of the conductor. Not all conductor configurations (e.g., coiled conductors, conductors formed into units, or the like) allow for exposure of the entire transverse circumference of the portion of the conductor where insulation is to be removed.

In some cases, the conductors may be pre-ablated prior to being disposed in the elongated member, thereby ensuring line-of-sight access to a complete circumference of the portion of the insulation to be removed. Aligning pre-ablated conductors, however, after the conductors have been disposed in the elongated member may require application of force to individual conductors. It may also be difficult to align the conductors if the ablation sites do not meet strict tolerances in positioning.

Additionally, some conductor configurations (e.g., conductors formed into units) are not conducive to pre-ablation. For example, when forming a coiled configuration of conductors it can sometimes be difficult to accurately position an ablated section within required tolerances. Typically, coiled configurations are formed with conductors being removed from spools and fed into a coiling machine. Ablation would need to be performed in the middle of this removal operation, thereby adding an additional layer of complexity.

In at least some embodiments, insulation may be removed from conductors after the conductors have been configured into a desired arrangement and disposed in the elongated member using a conductor-separating element ("separating element"). In at least some embodiments, the separating element is removably disposed over the outer layer of the elongated member and may be used to radially extend one or more conductors extending from the ends of the outer layer of the elongated member. The radially extended conductors may be retained in a radially-extended position such that portions of the conductors may be separated from one another and adequately exposed for ablative insulation removal. It will be understood that a separating element may be used with conductors disposed in the elongated member in many different configurations (e.g., arranged into units, coiled into a helical configuration, disposed in a multi-lumen device, disposed over a sleeve, disposed over a mandrel, or the like).

Figure 6A:
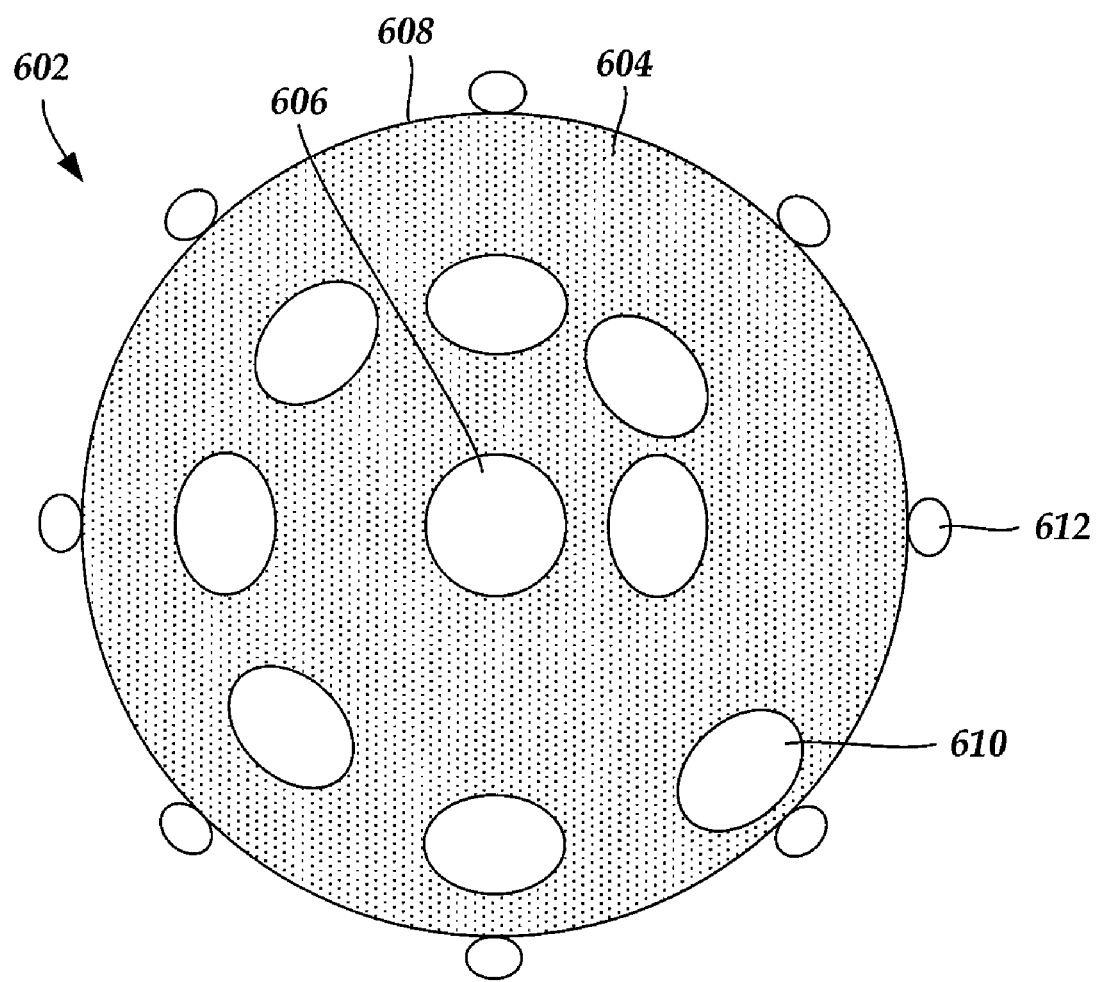
FIG. 6A is a schematic top view of one embodiment of a separating element for radially extending conductors of an elongated member, according to the invention.

FIG. 6A is a schematic top view of one embodiment of a separating element 602. The separating element 602 includes a body 604, a coupler 606, and an outer rim 608. A plurality of ablation windows, such as ablation window 610, are also defined in the body 604.

In at least some embodiments, the coupler 606 defines a mounting aperture configured and arranged to receive the elongated member. In at least some embodiments, the coupler 606 is configured and arranged to be positioned at either end of the outer layer of the elongated member. The coupler 606 may be positioned anywhere on the body 604. In preferred embodiments, the coupler 606 is located in proximity to the center of the body 604. In at least some embodiments, the coupler 606 includes a retention device (not shown) to retain the separating element 602 in position, when the separating element 602 is disposed over an elongated member.

The separating element 602 may have any transverse cross-sectional shape including, for example, triangular, square, pentagonal, hexagonal, heptagonal, octagonal, nonagonal, decagonal, circular, oval, or the like. In at least some embodiments, the separating element 602 has a non-geometric transverse cross-sectional shape. In a preferred embodiment, the separating element 602 has a circular transverse cross-sectional shape. In at least some embodiments, the separating element 602 is cone-shaped. The separating element 602 may be fabricated from any material that is rigid enough to retain conductors in a radially-extended position while insulation is removed from the conductors.

In at least some embodiments, retention devices (e.g., a clamp or the like), such as retention device 612, are positioned along the outer rim 608. The retention devices 612 may be used to retain the conductors in radially-extended positions when the conductors are extended along the lumens. In at least some embodiments, the body 604 may include one or more guide features (e.g., channels, clips, or the like) to guide a conductor across one or more of the ablation windows 610 to one of the retention devices 612.

In at least some embodiments, the ablation windows 610 extend through the body 604. In at least some embodiments, the ablation windows 610 are positioned such that, when one of the conductors is disposed along the separating element, the conductor extends across the ablation window, thereby providing line-of-sight access entirely around a transverse circumference of the portion of the conductor extending across the ablation window. In at least some embodiments, the ablation windows 610 are positioned such that, when one of the conductors is disposed in the separating element, the conductor extends across the ablation window, thereby providing adequate space to ablate (e.g., laser ablate or the like) a portion of the insulation encasing the conductor entirely around the transverse circumference of the conductor. In at least some embodiments, the ablation windows 610 are positioned such that, when one of the conductors is disposed in the separating element, the conductor extends across the ablation window, thereby providing enough space to electrically couple (e.g., laser weld, resistance weld, cut, swage, crimp, solder, or the like) the conductor to a terminal or electrode (or conductive contact) once an adequately-sized portion of the insulation has been removed.

The ablation windows 610 may be defined in the body 604 at any radial distance from the center of the body 604. The distance between the coupler 606 and a given ablation window 610 approximates the distance from the end of the outer layer of the elongated member that the insulation of the corresponding conductor is removed. In at least some embodiments, the ablation windows 610 are radially staggered so that, when the insulation is removed from the conductors, the exposed portions of the conductors are staggered so that terminals or electrodes (or conductive contacts) may be electrically coupled to the exposed portions of the conductors in a staggered arrangement.

The ablation windows 610 may have any transverse cross-sectional shape including, for example, triangular, square, pentagonal, hexagonal, heptagonal, octagonal, nonagonal, decagonal, circular, oval, or the like. In at least some embodiments, the ablation windows 610 have non-geometric transverse cross-sectional shapes.

It will be understood that the separating element may include many different ablation-window configurations. For example, each of the ablation windows may be defined at the same radial distance from the center of the body 604. In at least some embodiments, the radial positioning of one or more of the ablation windows may be adjustable so that the distance between the end of the elongated member and the removed portion of the insulation may be controlled.

Figure 6B:
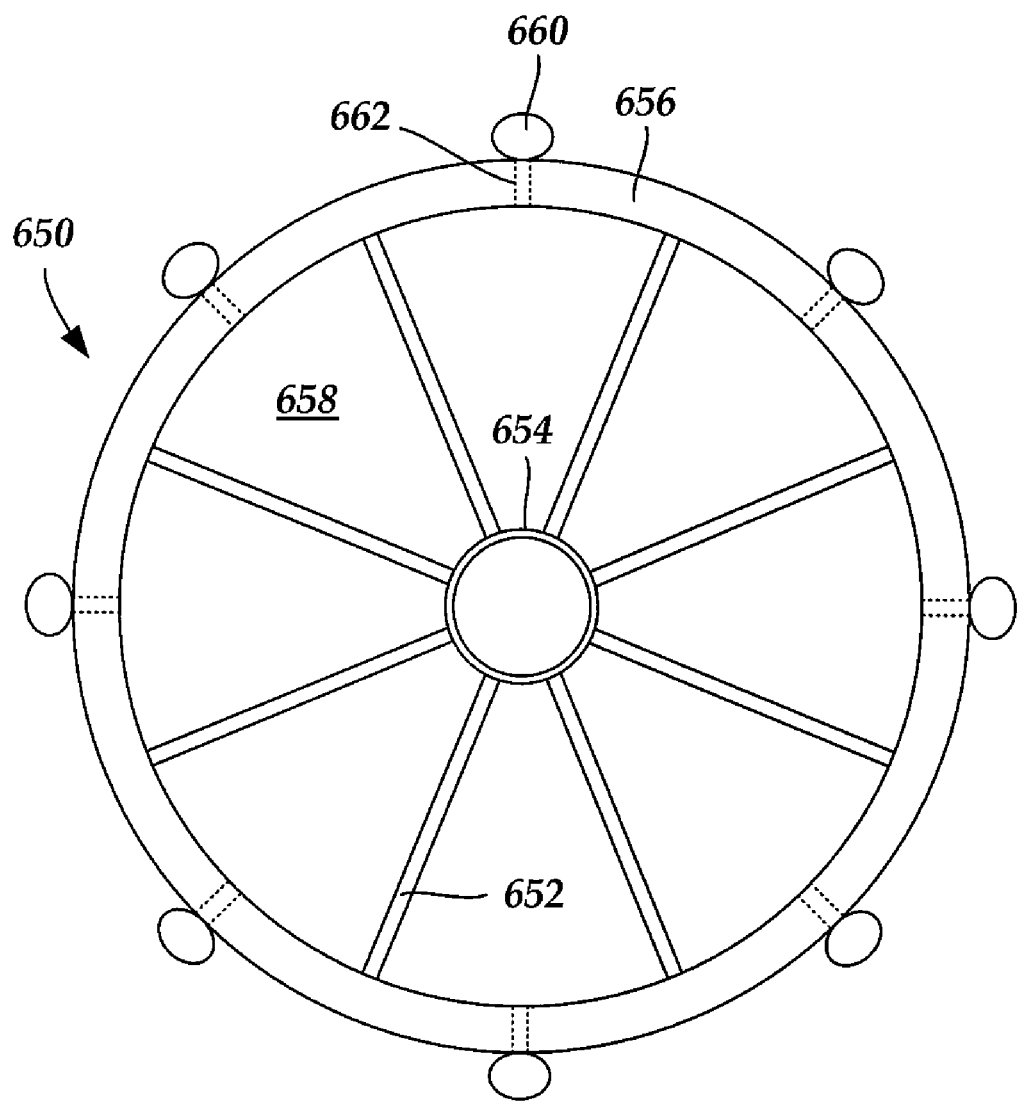
FIG. 6B is a schematic top view of another embodiment of a separating element for radially extending conductors of an elongated member, according to the invention.

It will be understood that the separating element may be formed in many different ways. For example, the body may include less material or the ablation windows may be larger-sized in relation to the size of the body, as compared to the ablation windows 610 and body 604 of FIG. 6A. FIG. 6B illustrates another embodiment of a separating element 650 having a body 652 that includes a plurality of spokes separating a coupler 654 from an outer rim 656. Ablation windows, such as ablation window 658 are defined by the coupler 654, the outer rim 656, and two adjacent spokes of the body 652. Thus, most of the longitudinal length of the conductors disposed in the separating element 650 may be accessible between the coupler 654 and the outer rim 656. In at least some embodiments, the separating element 650 includes retention devices, such as retention device 660, to retain the conductors in a radially-extended position when conductors are disposed in the separating element 650. In at least some embodiments, the outer rim 656 defines lumens, such as lumen 662, through which at least a portion of the conductors may extend when the conductors are disposed in the separating element 650. In at least some embodiments, the outer rim 656 does not include lumens.

It will be understood that the body 652 may include spokes that are non-isodiametric. For example, in at least some embodiments, the body 652 includes spokes that are triangular-shaped, thereby giving the body 652 a dartboard-like appearance.

The ablation windows 610 and 658 allow the conductors to be held in position such that portions of the insulation encasing a given conductor may be removed in relation to the other conductors. It may be an advantage to be able to remove insulation from one end of each of the conductors relative to one another to ensure proper placement of the insulation removal without having to push or pull a given conductor in or out of the elongated member to align removed insulation with the removed insulation of other conductors disposed in the elongated member.

Separating elements may be formed to accommodate many different numbers of conductors including, for example, one, two, three, four, five, six, seven, eight, nine, ten, twelve, sixteen, twenty, twenty-four, thirty, thirty-two, fifty, sixty-four or more conductors. It will be understood that separating elements may be formed to accommodate many other numbers of conductors, as well.

Figure 6C:
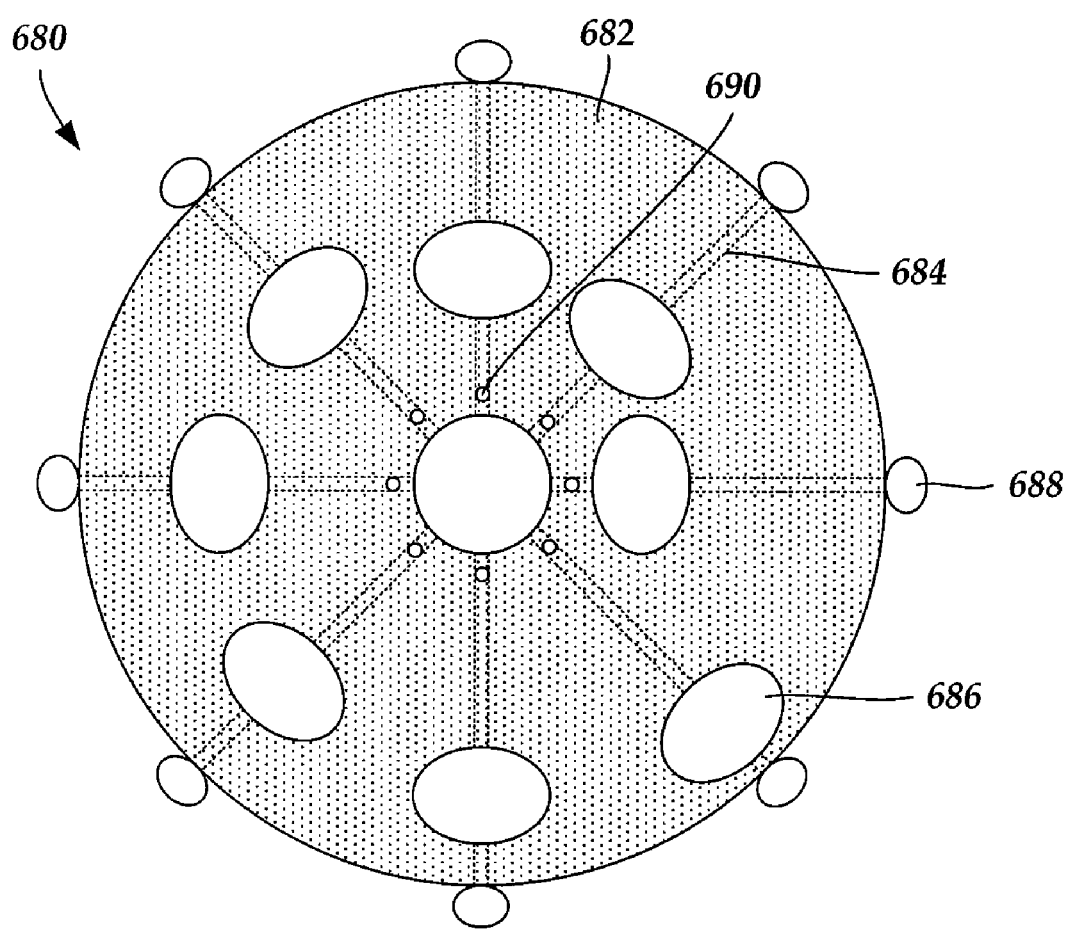
FIG. 6C is a schematic top view of yet another embodiment of a separating element for radially extending conductors of an elongated member, the separating element including lumens defined in a body of the separating element, according to the invention.

In at least some embodiments, the separating element may define one or more lumens through which one or more conductors may extend when a conductor is disposed on the separating element. FIG. 6C is a schematic top view of yet another embodiment of a separating element 680 having a body 682 that defines lumens, such as lumen 684, extending radially outward from a location in proximity to a center of the body 682. In at least some embodiments, the lumens 684 are configured and arranged to align with ablation windows, such as ablation window 686, defined in the body 682. In at least some embodiments, the lumens 684 are configured and arranged to align with retention devices, such as retention device 688, defined in the body 682.

In at least some embodiments, the lumens 684 are configured and arranged to receive the ends of the conductors disposed on the separating element. The lumens 684 are configured and arranged to separate the ends of each of the conductors from one another. In at least some embodiments, the lumens 684 extend from an insertion aperture, such as insertion aperture 690. The insertion aperture 690 may be anywhere along a length of the lumens 684. For example, in some embodiments the insertion apertures 690 are positioned in a center of the body 682. In other embodiments the insertion apertures 690 are positioned along the length of the lumens 684, either medial or lateral to the ablation windows 686.

In at least some embodiments, terminals or electrodes (or conductive contacts) can be electrically coupled to the conductors while the conductors are disposed in the separating element. Accordingly, it may be an advantage to have the insertion apertures 688 positioned lateral to the ablation windows 686 so that the conductors and electrically-coupled terminals or electrodes (or conductive contacts) can be removed from the separating element without needing to withdraw the electrically-coupled terminals or the electrodes (or conductive contacts) through the lumens.

Figure 7A:
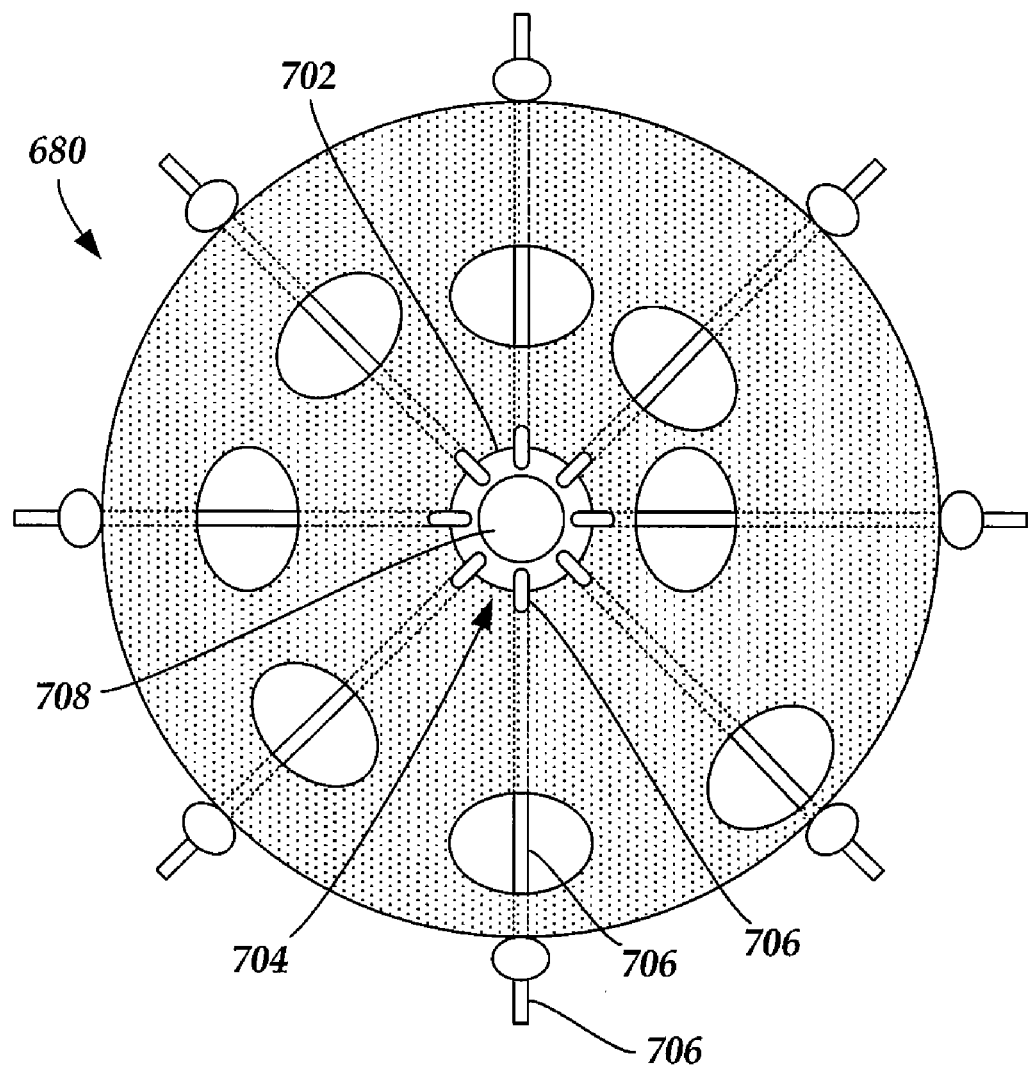
FIG. 7A is a schematic top view of one embodiment of the separating element of FIG. 6A coupled to one end of an elongated member having conductors that are being radially extended by the separating element, according to the invention.
Figure 7B:
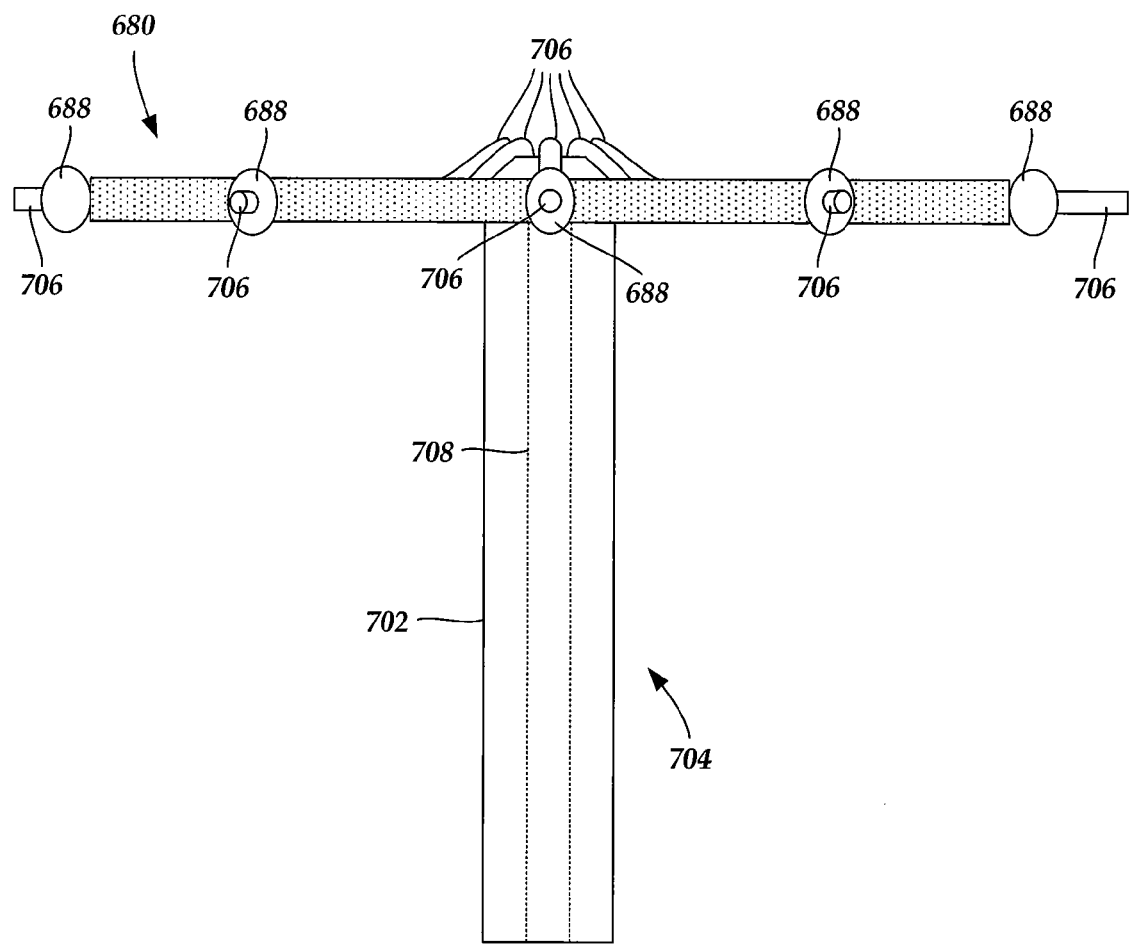
FIG. 7B is a schematic side view of one embodiment of the separating element of FIG. 6A coupled to one end of the elongated member of FIG. 7A having conductors that are being radially extended by the separating element, according to the invention.
Figure 7C:
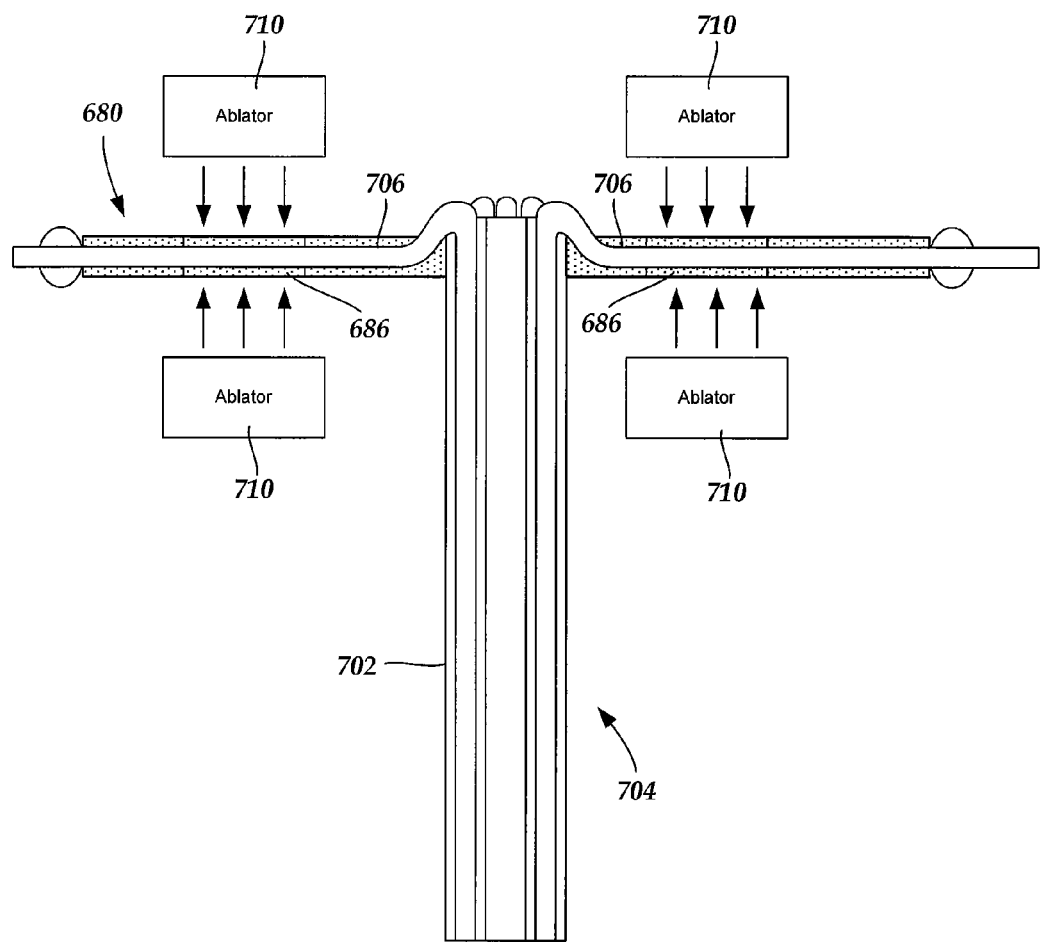
FIG. 7C is a schematic cross-sectional view of one embodiment of the separating element of FIG. 6A coupled to one end of the elongated member of FIG. 7A having conductors that are being radially extended by the separating element to expose portions of the conductors for insulation removal by ablators, according to the invention.

FIGS. 7A-7C illustrate conductors of an elongated member disposed in the separating element 680. Accordingly, the conductors are shown disposed in lumens defined in the body. It will be understood that conductors may similarly be disposed along the separating elements 602 and 650. The separating element 602, however, does not include lumens. Thus, conductors are disposed along a surface of the body 604 instead of being disposed within lumens.

FIG. 7A is a schematic top view of one embodiment of the separating element 680 coupled to one end of an outer layer 702 of an elongated member 704. A plurality of conductors, such as conductor 706, are disposed in the elongated member 704. The ends of the conductors 706 are inserted into lumens of the separating element 680 and radially extended outward from the outer layer 702 of the elongated member 704.

As discussed above, the separating element 680 may be used to spread and expose conductors 706 extending from one end of the outer layer 702 of the elongated member 704 to facilitate removal of the layer of insulation encasing each of the conductors 706. The conductors 706 may be disposed in the elongated member 704 in many different configurations (e.g., arranged into units, coiled into a helical configuration, disposed in a multi-lumen device, disposed over a sleeve, disposed over a mandrel, or the like). In FIG. 7A, the portions of the conductors 706 disposed in the elongated member 704 are shown wrapped around a sleeve or a mandrel 708.

FIG. 7B is a schematic side view of one embodiment of the separating element 680 disposed over one end of the outer layer 702 of the elongated member 704. The plurality of conductors 706 are disposed in the elongated member 704. Each of the conductors 706 extends through a different one of the retention devices 688 of the separating element 680, thereby radially extending the conductors 706 from the elongated member 704.

FIG. 7C is a schematic cross-sectional view of one embodiment of the separating element 680 disposed over one end of the outer layer 702 of the elongated member 704. The conductors 706 are extending radially outward from the elongated member 704 and are separated from one another. One or more ablators 710 are positioned in proximity to ablation windows 686 defined in the separating element 680. In preferred embodiments and as shown in FIG. 7C, the conductors 706 extend across the ablation windows 686 such that the complete circumference of the portion of the insulation to be removed from the conductors 706 is accessible by the ablators 710.

In at least some embodiments, the elongated member may be formed by disposing conductors into the elongated member such that the proximal ends of the conductors extend outward from a proximal end of the outer layer of the elongated member and the distal ends of the conductors extend outward from a distal end of the outer layer. The coupler of the separating element is disposed over the proximal end of the outer layer of the elongated member. The conductors are disposed in the separating element such that the conductors extend radially-outward from the elongated member, extending across ablation windows. In at least some embodiments, the ends of the conductors are held in position by retention devices disposed in proximity to the outer rim of the separating device. Portion of the layers of insulation encasing the conductors are removed in the regions of the conductors spanning the ablation windows of the separating element. In at least some embodiments, when one end of the conductors are disposed in the separating element and retained by one of the retention devices, tension may be applied to the conductors along a portion of the conductors not disposed on the separating element to pull the conductors tight across the ablation windows, thereby reducing sag across the ablation windows.

In at least some embodiments, the separating element is then removed from the proximal end of the elongated member and further processing of the conductors may be performed. For example, terminals are electrically coupled (e.g., laser welded, resistance welded, cut, swaged, crimped, soldered, or the like) to the portions of the conductors exposed by the removed insulation. In at least some other embodiments, the terminals are electrically coupled to the conductors while the conductors are still disposed in the separating element, and the conductors are subsequently removed from the proximal end of the elongated member.

Once the separating element is removed from the proximal end of the elongated member, the separating element may be disposed on the distal end of the elongated member and the same process is performed with the distal end of the conductors. Electrodes (or conductive contacts), however, are electrically coupled to the distal end of the conductors instead of terminals.

In at least some embodiments, the layers of insulation are removed from the conductors by laser ablation. In at least some embodiments, the separating element (with conductors disposed in the separating element) is configured and arranged for placement in a laser ablation system. In at least some embodiments, the laser ablation system may be configured and arranged to automatically remove insulation from desired conductors at desired locations.

Figure 8:
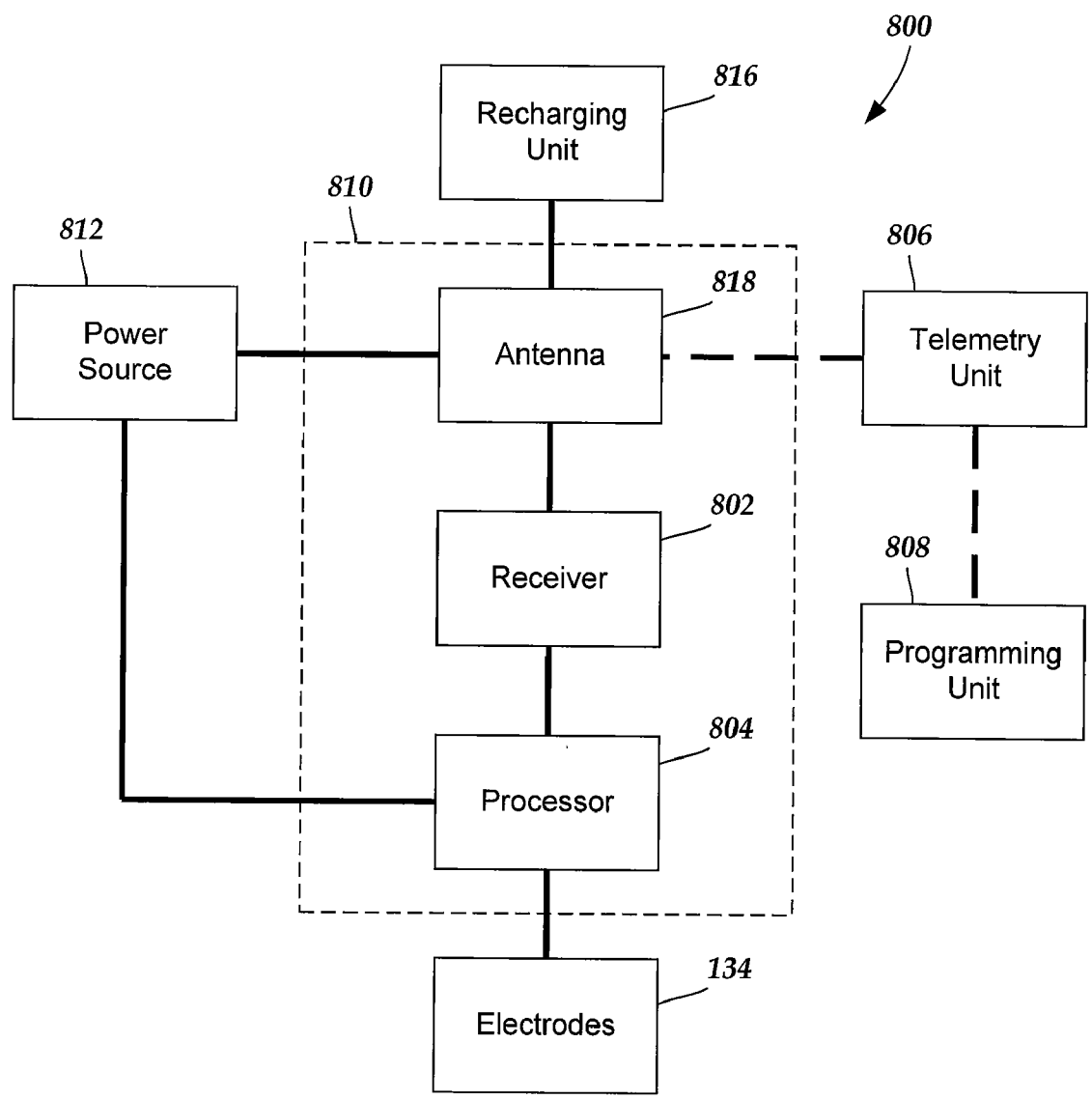
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for forming a lead or lead extension, the method comprising:
    forming an arrangement of a plurality of elongated conductors, each conductor extending from a proximal end of the arrangement to a distal end of the arrangement, each of the plurality of conductors is a wire that comprises a layer of insulation disposed over a conductive core; the plurality of conductors comprising a first conductor;
    disposing a conductor-separating element over the proximal end of the arrangement, the conductor-separating element comprising a plurality of windows defined in a body, the plurality of windows comprising a first window;
    radially extending a proximal end of the first conductor over a portion of the conductor-separating element such that a portion of the first conductor extends across, and is exposed through, the first window of the conductor-separating element;
    directing ablation energy through the first window to ablate insulation from the portion of the first conductor extending across the first window in order to expose a portion of the conductive core of the first conductor; and
    removing the conductor-separating element from the proximal end of the arrangement of the plurality of elongated conductors.

2. The method of claim 1, further comprising electrically coupling the exposed portion of the conductive core of the first conductor to one of a terminal, an electrode, or a conductive contact.

3. The method of claim 2, wherein electrically coupling the exposed portion of the conductive core of the first conductor to one of a terminal, an electrode, or a conductive contact is performed while the proximal end of the first conductor remains radially extended along the conductor-separating element.

4. The method of claim 1, further comprising after removing the the conductor-separating element from the proximal end of the arrangement, disposing the conductor-separating element over the distal end of the arrangement.

5. The method of claim 4, further comprising radially extending a distal end of the first conductor along the conductor-separating element such that a portion of the first conductor extends across one of the windows of the conductor-separating element.

6. The method of claim 5, further comprising ablating insulation from the portion of the first conductor extending across the one of the windows to expose a portion of the conductive core of the first conductor.

7. The method of claim 1, wherein ablating insulation from the portion of the first conductor comprises laser ablating the insulation.

8. The method of claim 7, wherein laser ablating the insulation from the portion of the first conductor comprises using a laser ablation system to laser ablate the insulation.

9. The method of claim 1, wherein radially extending the proximal end of the first conductor along the conductor-separating element comprises extending the proximal end of the first conductor across the first window such that access through the window is provided entirely around a circumference of the first conductor.

10. The method of claim 1, wherein ablating insulation from the portion of the first conductor extending across the first window comprises ablating the insulation entirely around a circumference of the first conductor.

11. The method of claim 1, wherein the conductor-separating element comprises at least one retention device configured and arranged to retain the first conductor in a radially-extended position.

12. The method of claim 1, wherein the body of the conductor-separating element defines a lumen configured and arranged to receive the first conductor.

13. The method of claim 12, wherein the lumen extends radially along the body of the conductor-separating element from a lateral end of the first window to an outer rim of the body.

14. The method of claim 1, wherein the conductor-separating element has a round transverse cross-sectional shape.

15. The method of claim 1, wherein disposing the conductor-separating element over the proximal end of the arrangement comprises disposing a coupler of the conductor-separating element over a portion of the arrangement.

16. The method of claim 15, wherein the coupler comprises a mounting aperture defined in the body.

17. The method of claim 16, wherein the mounting aperture is defined in the center of the body.

18. The method of claim 1, wherein the conductor-separating element comprises:
   the body defining an outer rim and the plurality of windows disposed circumferentially around the body;
   a mounting aperture configured and arranged to receive the plurality of elongated conductors, the mounting aperture positioned in a center of the body;
   a plurality of retention devices disposed around the outer rim of the body, each retention device configured and arranged to receive, and retain, an end of one of the conductors which passes through the center aperture and is bent over, and extended along, the body of the conductor-separating element,
   wherein the plurality of windows are positioned such that, when the end of one of the conductors is extended along the body of the conductor-separating element and received in a one of the retention devices, the conductor has a portion that is exposed through at least one of the windows.

19. The method of claim 1, where each of the plurality of elongated conductors is multi-filar.

20. The method of claim 1, wherein each of the plurality of elongated conductors is a single filament.

* * * * *